(12) United States Patent
Welter

(10) Patent No.: US 7,150,900 B2
(45) Date of Patent: *Dec. 19, 2006

(54) LIQUID-CRYSTAL COMPOSITIONS COMPRISING CHIRAL COMPOUNDS

(75) Inventor: Thomas R. Welter, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 283 days.

This patent is subject to a terminal disclaimer.

(21) Appl. No.: 10/737,457

(22) Filed: Dec. 16, 2003

(65) Prior Publication Data

US 2005/0127327 A1    Jun. 16, 2005

(51) Int. Cl.
*C09K 19/52* (2006.01)
*C09K 19/38* (2006.01)
*C09K 19/54* (2006.01)
*C09K 19/58* (2006.01)

(52) U.S. Cl. .................. 428/1.3; 428/1.1; 252/299.01; 252/299.2; 252/299.5

(58) Field of Classification Search ................ 428/1.1, 428/1.3; 252/299.01, 299.2, 299.5
See application file for complete search history.

(56) References Cited

U.S. PATENT DOCUMENTS

| 3,945,968 | A | 3/1976 | Goletto |
| 4,346,167 | A | 8/1982 | Imatomi et al. |
| 4,895,793 | A | 1/1990 | Seto et al. |
| 5,053,555 | A | 10/1991 | Yeager et al. |
| 7,052,743 | B1 * | 5/2006 | Welter et al. ........... 252/299.01 |
| 2005/0072961 | A1 * | 4/2005 | Welter et al. ........... 252/299.01 |

FOREIGN PATENT DOCUMENTS

| EP | 0 307 951 | | 3/1989 |
| JP | 63-63719 | * | 3/1988 |

OTHER PUBLICATIONS

English abstract for JP 63-63719, 1988.*
U.S. Appl. No. 10/651,692 08/2003 Welter et al.
Bernhard Kohler et al., "Novel Chiral Macrocycles Containing Two Electronically Interacting Arylene Chromophores," Chem. Eur. J. 2001, 7, No. 14.
Giovanni Gottarelli and Gian P. Spada, "Induced Cholesteric Mesophases: Origin and Application," Mol. Cryst. Liq. Cryst., 1985, vol. 123, pp. 377-388.
Gian Piero Spada and Gloria Proni, "The nematic Liquid Crystal Phase as a Probe of the Molecular Shape Helicity," Enautiomer, vol. 3, pp. 301-314.
Zvonimir Dogic and Seth Fraden, "Cholesteric Phase in Virus Suspensions," Langmuir 2000,16, 7820-7824.
Birman V. B. et al., "1,1'-Spirobiindane-7,7'-diol: a novel, C2-symmetric chiral ligand"Tetrahedron: Asymmetry, Elsevier Science Publishers, Amsterdam, NL, vol. 10, 1999, pp. 125-131.

* cited by examiner

*Primary Examiner*—Shean C. Wu
(74) *Attorney, Agent, or Firm*—Chris P. Konkol

(57) ABSTRACT

The invention relates to a class of compounds useful as chiral dopants, which compounds are available in both enantiomeric forms, in liquid-crystal formulations. Such formulations are advantageous in displays and various other products.

15 Claims, No Drawings

LIQUID-CRYSTAL COMPOSITIONS COMPRISING CHIRAL COMPOUNDS

FIELD OF THE INVENTION

The present invention involves the formation of chiral-nematic liquid-crystal (LC) compositions using nematic materials in combination with chiral dopants.

BACKGROUND OF THE INVENTION

Chiral-nematic, also known as cholesteric, liquid-crystalline materials are useful in a variety of applications including various LC display components, reflective films, optical filters, polarizers, paints, and inks, among others. Methods for preparing such materials are well established. See, e.g., Giovanni Gottarelli and Gian P. Spada, *Mol. Cryst. Liq. Crys.*, Vol. 123, pp. 377–388 (1985); Gian Piero Spada and Gloria Proni, *Enantiomer*, Vol. 3, pp. 301–314 (1998). However, improvement is still needed. While early uses of chiral-nematic compositions relied upon mixtures composed mostly of chiral components, more recently such materials are composed of nematic LC mixtures combined with small amounts of chiral dopants. In such new compositions the properties of the nematic host material, for example viscosity, birefringence, electrical anisotropy, and magnetic anisotropy among others, are tailored to the desired usage by altering the chemical composition of the nematic mixture, and then a chiral dopant is incorporated to induce helical twisting so as to provide the desire chiral-nematic pitch. It is apparent that the properties of this chiral nematic composition are therefore a combination of the properties of the nematic host plus those of the dopant. It is further well understood that by reducing the amount of dopant, the properties of the host nematic LC formulation might be better preserved. Certainly, reducing the concentration of a specific dopant also reduces the pitch of the resulting chiral-nematic formulation. Many uses of chiral-nematic compositions require the formulation to reflect or transmit visible light, thus requiring compositions with substantial helical twist, i.e. short helical pitch ("p"). These considerations indicate that dopants that induce large amounts of nematic helical twist per unit concentration are prized. The figure of merit for such materials is its Helical Twisting Power ("HTP" or $\beta$).

A dopant material's HTP ($\beta$) is defined, in a specified host at a particular temperature, by Equation 1:

$$\beta = (pcr)^{-1} \qquad \text{(Equation 1)}$$

wherein the "p" is the measured helical pitch of the doped nematic ($\mu m$); "c" is the measure of the dopant concentration (usually in terms of mole fraction, weight fraction, or weight percent on a unitless scale, wherein mole fraction and weight fraction is on a scale of 0 to 1); and "r" is the enantiomeric excess of the dopant (on a unitless scale of 0 to 1). Enantiomeric excess (r) is defined as the absolute value of the difference in mole fraction (F) of the two enantiomer in a sample r equals $|F_{(+)} - F_{(-)}|$. Thus, for a racemic mixture r equals $|0.5-0.5|=0$; for an enantiomerically pure material r equals $|1.0-0|=1$; and for a 75% pure mixture the r equals $|0.75-0.25|=0.5$. The larger the HTP the lower the concentration of dopant needed to provide a specific pitch, and thereby yield a particular reflectance or transmission. The pitch of a chiral-nematic formulation can be measured using a variety of optical techniques. For example, see Zvonimir Dogic and Seth Fraden, *Langmuir*, Vol. 16, pp. 7820–7824 (2000). The dopant concentration is as formulated and the enantiomeric excess can be measured via chiral high-performance liquid chromatography (HPLC) or nuclear magnetic resonance (NMR) spectroscopy. Typically, for useful enantiomerically pure dopants, their HTP's range from one to several hundred ($\mu m^{-1}$). Dopants with twisting power greater than 100 (based on dopant mole fraction) are often described as "high twist" dopants. The discovery of new dopants, particularly high twist dopants, is important to broadening the utility of chiral-nematic formulations.

Not only can chiral-nematic liquid crystals be formulated to reflect various wavelengths of incident electromagnetic radiation, but it is well understood that reflected light is circularly polarized, depending upon the sense of chirality of the helical pitch. Thus, a chiral nematic displaying a right-handed helical mesostructure will reflect right-handed incident light. For many applications it is useful to be able to reflect both right-handed and left-handed senses of circularly polarized light, for example, in a vertically layered structure. It is further well known that enantiomers of a chiral-dopant structure induce the opposite polarity of helical rotation and, therefore, afford oppositely polarized light reflections. For this reason the preparation of enantiomeric pairs of dopants for use in separate light modulating layers can be particularly useful.

There are three general sources for obtaining substantially enantiomerically pure organic compounds for use as dopants or more likely as synthetic precursors for dopants: (1) compounds available from natural sources; (2) the preparative separation of racemic mixtures of enantiomers; or (3) chiral synthetic methods that directly afford desired enantiomers. Most commonly, only the latter two methods provide access to both enantiomers of a potential dopant. Natural sources generally provide only one of any enantiomeric pair, reflecting the fundamental chirality of life. Thus, using natural sources for dopants or their precursors can lead to limitations in dopant utility. A discovery of new dopants available from non-natural sources would therefore be especially useful.

SUMMARY OF THE INVENTION

Applicants have found a class of compounds useful as chiral dopants, which compounds are available in both enantiomeric forms. Another aspect of the invention relates to chiral-nematic liquid-crystal formulations comprising such chiral dopants. Such formulations are useful in displays and other products. Optionally, the chiral dopants can be capable of polymerization.

DETAILED DESCRIPTION OF THE INVENTION

We have found that certain compounds represented by the following Structure 1 are useful as a source of chiral dopants. In particular, the enantiomerically enriched form of such compounds, including the substantially enantiomerically pure form, introduced into nematic compositions, afford useful chiral nematic mixtures.

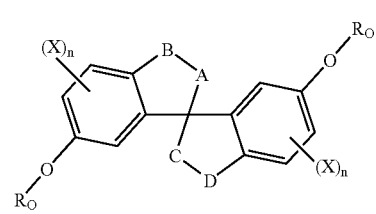

As evident, compounds of Structure 1 comprise a central nucleus comprising a spirodiphenoxy moiety. In Structure 1, A, B, C, and D are independent divalent groups; each X is any independently selected ring substituent, or X can form a fused ring with another X or $R_O$; n independently varies from 0 to 3, and the $R_O$ groups are independently selected from hydrogen or any substituent capping the phenolic oxygen in Structure 1. Preferably, A, B, C, and D are such that A and B comprise a first five or six-membered ring, and C and D comprise a second five or six-membered ring which rings share a spirocarbon atom to which A and C are attached.

A preferred embodiment is represented by the following Structure 2: wherein $R_{CO}$ is any suitable substituent, each X is any independently selected ring substituent or hydrogen, and $R_1$ and $R_2$ groups are independently hydrogen or an alkyl substituent.

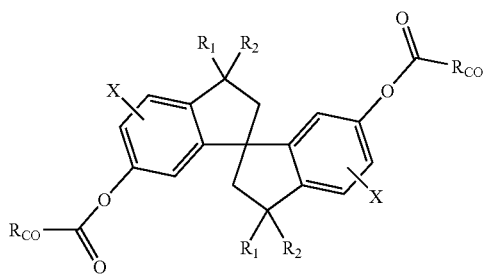

2

In general, when reference in this application is made to a particular moiety or group it is to be understood that such reference encompasses that moiety whether unsubstituted or substituted with one or more substituents (up to the maximum possible number. For example, "alkyl" or "alkyl group" refers to substituted or unsubstituted alkyl, while "benzene group" refers to a substituted or unsubstituted benzene (with up to six substituents). Generally, unless otherwise specifically stated, substituent groups usable on molecules herein include any groups, whether substituted or unsubstituted, which do not destroy properties necessary for mesophase utility. Examples of substituents on any of the mentioned groups can include known substituents, such as: chloro, fluoro, bromo, iodo; hydroxy; alkoxy, particularly those "lower alkyl" (that is, with 1 to 12 carbon atoms, for example, methoxy, ethoxy; substituted or unsubstituted alkyl, particularly lower alkyl (for example, methyl, trifluoromethyl); thioalkyl (for example, methylthio or ethylthio), particularly either of those with 1 to 12 carbon atoms; substituted or unsubstituted alkenyl, preferably of 2 to 12 carbon atoms (for example, ethenyl, propenyl, or butenyl); substituted and unsubstituted aryl, particularly those having from 6 to 20 carbon atoms (for example, phenyl); and substituted or unsubstituted heteroaryl, particularly those having a 5 or 6-membered ring containing 1 to 3 heteroatoms selected from N, O, or S (for example, pyridyl, thienyl, furyl, pyrrolyl); acid or acid salt groups; such groups as hydroxyl, amino, alkylamino, cyano, nitro, carboxy, carboxylate, acyl, alkoxycarbonyl, aminocarbonyl, sulfonamido, sulfamoyl, sulfo, sulfonate, or alkylammonium; and other groups known in the art. Alkyl substituents may specifically include "lower alkyl" (that is, having 1–12 carbon atoms), for example, methyl, ethyl, and the like. Further, with regard to any alkyl group or alkylene group, it will be understood that these can be branched or unbranched and include ring structures.

In general, when reference herein is made to the formation of a ring or rings between various structural elements or groups of Structure 1, this should be understood as excluding from the definition of Structure 1 macrocyclic compounds including two or more structural units based on Structure 1 connected to each other in a ring. Such macrocyclic compounds are specifically excluded from this invention. However, linear oligomeric structures containing two or more structural units based on Structure 1 are not so excluded, wherein a structural unit based on Structure 1 are defined as a bivalent moiety obtained from a compound of Structure 1 by the removal of a hydrogen from two groups in the compound of Structure 1 to form two connecting bonds on opposite sides of the compound from the two rings containing the spiro carbon in the structural unit. Such excluded macrocyclic compounds are disclosed by Köhler, Bernhard et al. in "Novel Chiral Macrocyles containing Two Electronically Interacting Arylene Chromophores," *Chem. Eur. J.* 2001, 7, No. 14. Compounds of Structure 1 are disclosed for making such macrocyclic compounds, but only the macrocyclic compound is disclosed as useful chiral dopants in liquid crystal compositions.

A, B, C, and D in Structure 1 can independently be any bivalent substituent such as methylene, oxygen, sulfur, sulfoxyl, sulfonyl, carbonyl, mono-substituted nitrogen (N—R), di-substituted carbon ($R_1$—C—$R_2$), wherein R, $R_1$ and $R_2$ are independently hydrogen or any substituent. It is preferred the A, B, C, and D independently be methylene or di-substituted carbon ($R_1$—C—$R_2$). It is more preferred that both A or B (and/or C or D) be methylene or di-substituted carbon ($R_1$—C—$R_2$). In one embodiment, A and B are the same, respectively as C and D. R, R and R' can independently be the same as X. Organic carbon-containing substituents having 1 to 12 carbon atoms are preferred.

The X substituent in Structure 1 can be any substituent. It is preferred to be an oxygen-containing organic substituent and/or a carbon-containing substituent. Preferred oxygen-containing substituents include alkoxy, aryloxy, carboalkyl (O—C(=O)R), carboaryl (O—C(=O)Ar), carboalkoxy (O—C(=O)OR), carboaryloxy (O—C(=O)OAr) either substituted or unsubstituted. Preferred carbon-containing substituents include alkyl groups of about 1–20 carbons, cycloalkyl groups of about 1–20 carbons, aryl groups of about 6–20 carbons, alkaryl groups of about 6–20 carbons, and heterocyclic groups having at least one heteroatom and 2–20 carbons; all either substituted or unsubstituted. Other preferred oxygen-containing organic substituents include carboalkoxy (C—C(=O)OR), carboaryloxy (C—C(=O)OAr), aryl or alkyl ketones (C—C(=O)R) or (C—C(=O)Ar), all either substituted or unsubstituted. Other suitable X substituents include, but are not limited to halogens; cyano (—CN); hydroxyl, amino, alkylamino, cyano, nitro, carboxy, aminocarbonyl, sulfonamido, sulfamoyl, sulfo, sulfonate, or alkylammonium; as well as a siloxane residue or polymerizable groups as mentioned below. Preferably, an X group meeting the definition of —$OR_O$ is not located on both aromatic rings in Structure 1 in a position adjacent each ring containing the spiro carbon (i.e., substituted on an aromatic carbon bonded to said ring). Spirodiphenol derivatives having an —$OR_O$ group in such a position (in the 7,7' position as compared to the 6,6' position) are disclosed in copending, commonly assigned U.S. Ser. No. 10/651,692, filed Aug. 29, 2003 by Welter et al., hereby incorporated by reference.

Furthermore, any two members of the following set: X and $R_O$ on the same aromatic ring in Structure 1 may be joined to form a fused ring, either aliphatic, unsaturated or aromatic provided that creation of the ring will not interfere with the functioning of the chiral dopant.

In one preferred embodiment of Structure 1, both "n" subscripts are 0 or 1.

The $R_O$ group in Structure 1 is independently any substituent or hydrogen, preferably having 1 to 24 carbon atoms, more preferably 8 to 18 carbon atoms. It is preferred to be alkyl, cycloalkyl, aryl, aralkyl, carbonyl such as alkylcarbonyl, arylcarbonyl, alkoxycarbonyl, aryloxycarbonyl, alkylsulfoxy, or arylsulfonyl, substituted or unsubstituted. It is more preferred to be carbonyl, $C(=O)R_{CO}$, where $R_{CO}$ is aryl, alkyl, cycloalkyl, or alkaryl, or heterocyclic either substituted or unsubstituted. It is particularly preferred for the $R_{CO}$ group to contain an aromatic ring, for example, a phenyl-containing group. It is most preferred that $R_{CO}$ be aryl either substituted or unsubstituted as defined by: $-R_{CO}=-(Y-L)_m-Z$: wherein L is a single bond e.g. $-(Y)_m-Z$ or bivalent linking group chosen from the following groups: $-C(=O)O-$; $-OC(=O)-$; $-CH_2CH_2-$; $-CH=CH-$; $-C\equiv C-$; $-OCH_2-$; $-CH_2O-$; $-N=CH-$; $-CH=N-$; $-OC(=O)O-$; $-C\equiv C-C\equiv C-$; $-COCH=CH-$; $-CH=CHCO-$; $-O-$; $-S-$; -and $SO_2$; wherein Y and Z independently may be 1,4-phenylene in which, in addition, one or more methylene may be replaced by $-N=$, 1,4-cyclohexyl in which, in addition, one or more non-adjacent methylene units may be replaced by O or S, 1,4-cyclohexylene, 1,4-bicyclo[2.2.2]octylene, piperidine-1,4-diyl, naphthalene-1,6-diyl, dechydronaphthalene-1,6-diyl, 1,2,3,4-tetrahydronaphthalene-1,6-diyl, in which each of these groups be unsubstituted or mono-substituted or poly-substituted with halogen, cyano, isocyanato, or nitro groups; or alkyl, alkoxyl or alkanoyl groups bearing 1–12 carbons where one or more hydrogens may be substituted with chlorine or fluorine and wherein m=0, 1, 2, 3, 4. As indicated above, $R_0$ can form a fused ring with an X group. The two $R_0$ groups in Structure 1 (or the two RCO groups in Structure 2) can also be connected to form a bridge between the two phenyl rings in, respectively, Structure 1 or Structure 2.

A few examples of compounds according to the present invention, which examples are merely illustrative and not intended to be limiting, are as follows:

I-1
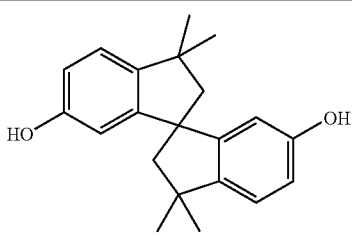

I-2
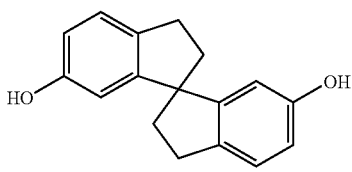

I-3
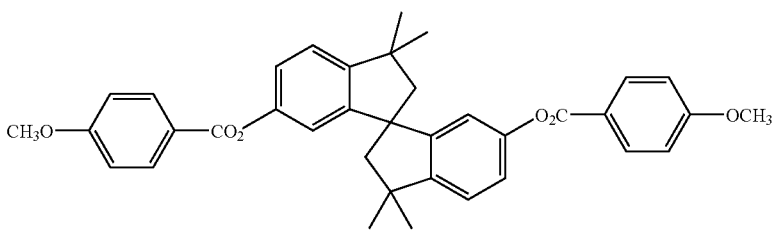

I-4
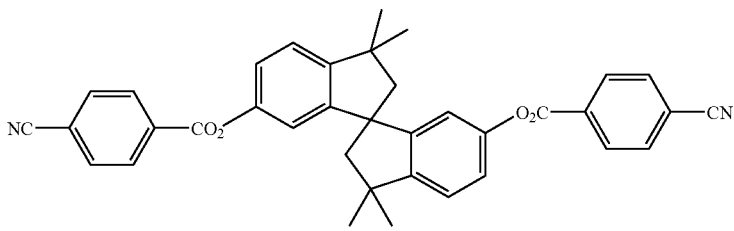

I-5
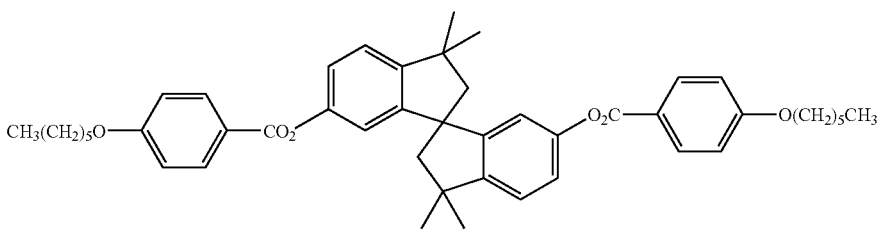

-continued
I-6
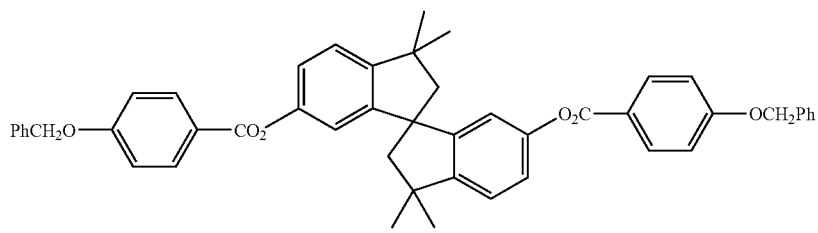
I-7
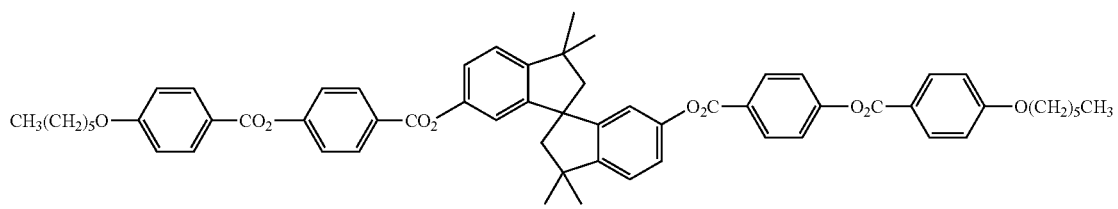
I-8
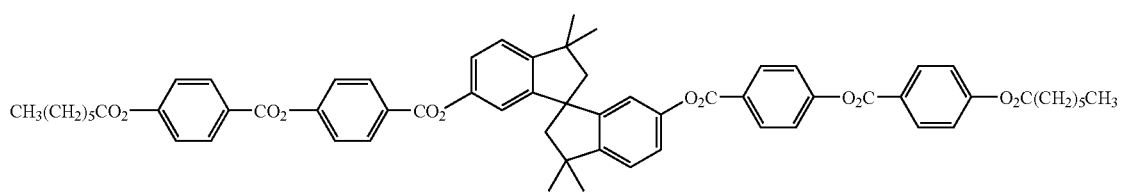
I-9
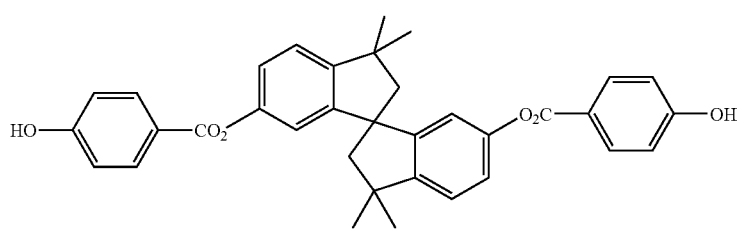
I-10
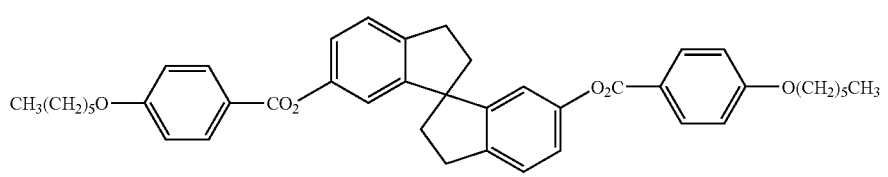
I-11
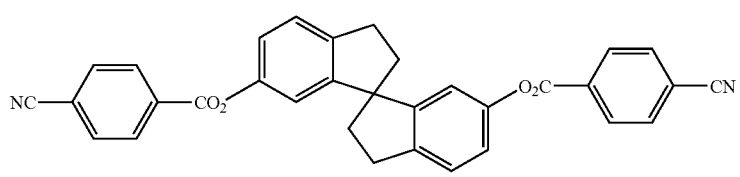
I-12
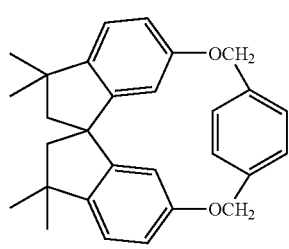

-continued
I-13
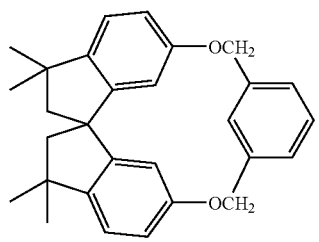
I-14
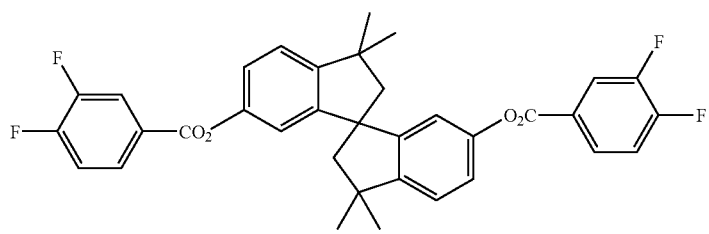
I-15
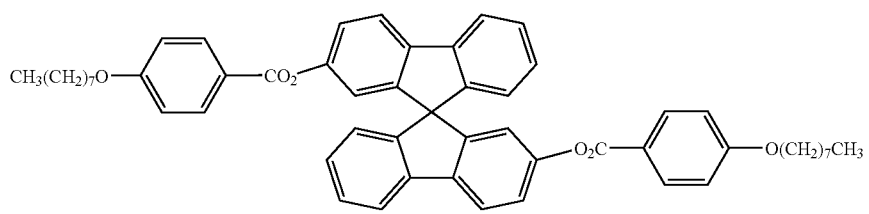
I-16
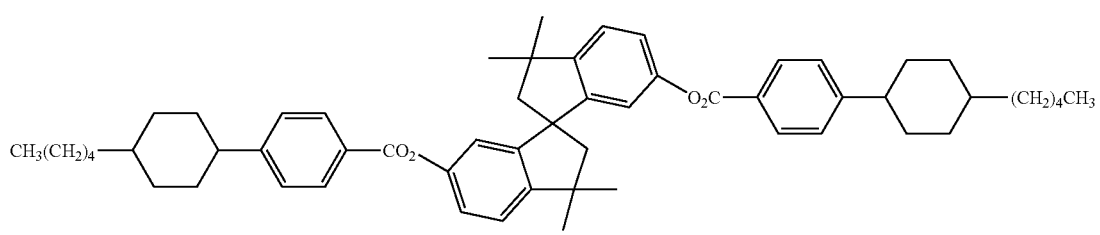
I-17
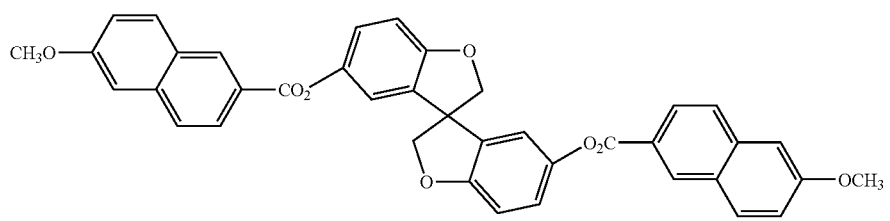
I-18
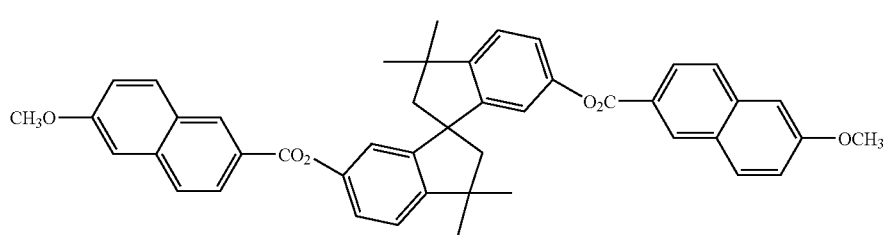
I-19
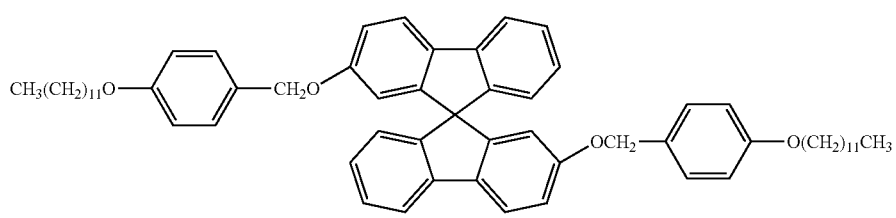

-continued
I-20
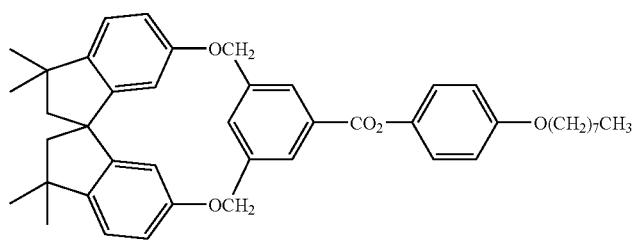
I-21
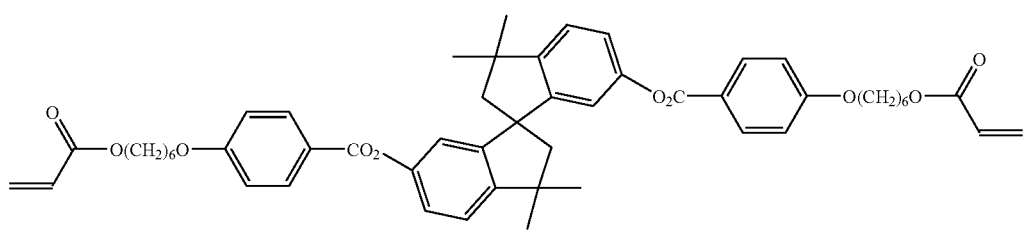
I-22
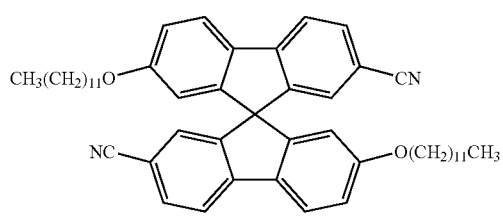
I-23
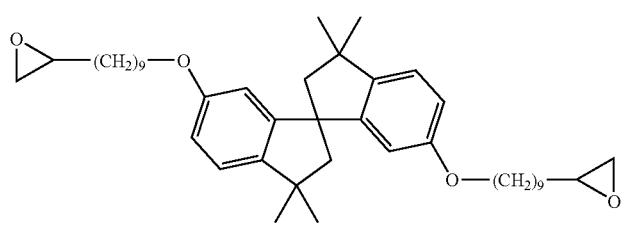
I-24
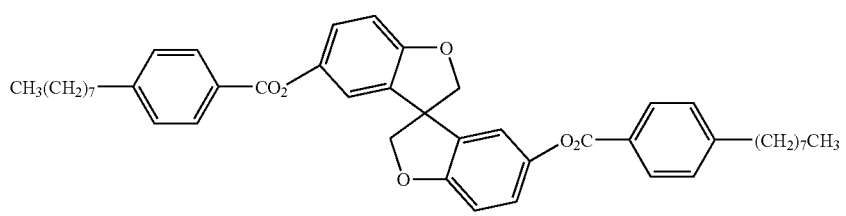
I-25
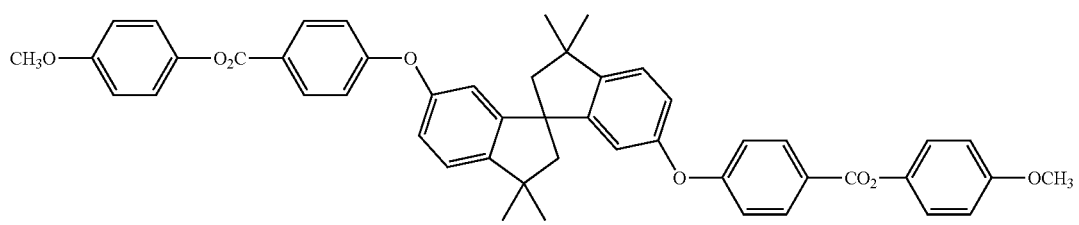
I-26
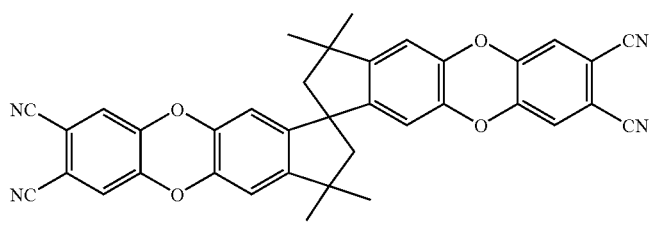

-continued
I-27
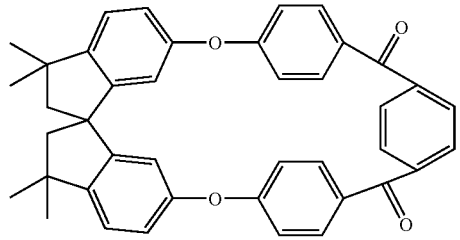
I-28
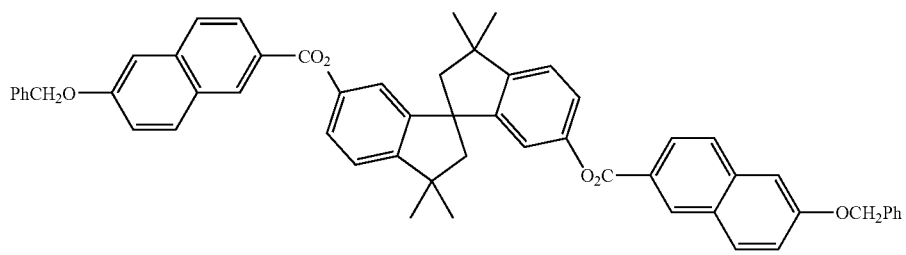
I-29
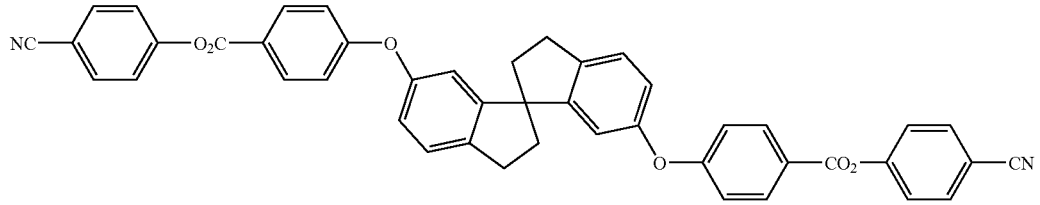
I-30
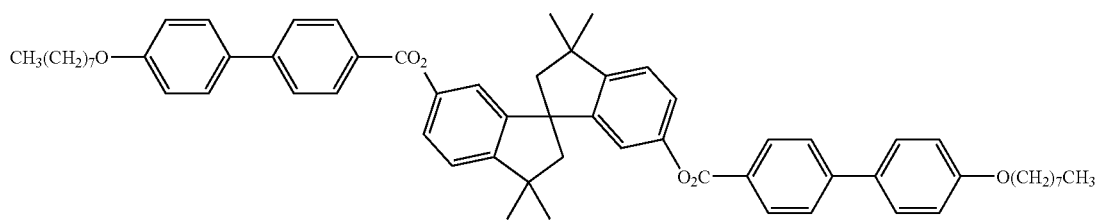
I-31
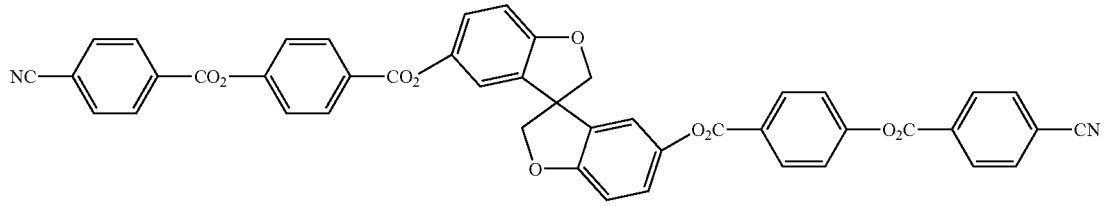
I-32
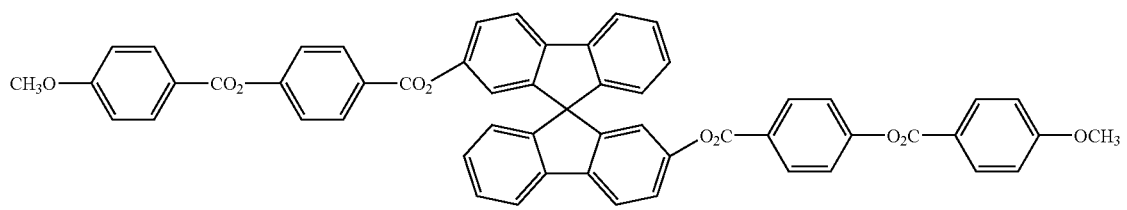
I-33
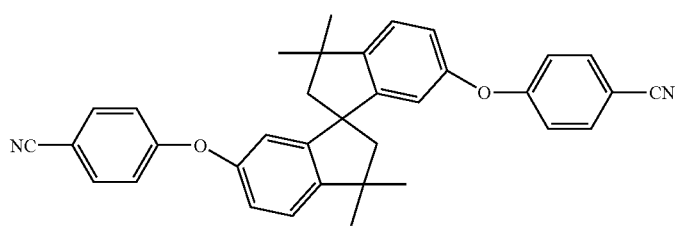

In a further embodiment, the dopant compound of Structure 1 or Structure 2 may contain as a part of A, B, C, D, X, $R_O$, $R_{CO}$, R, $R_1$, $R_2$, Y, and/or Z a polymerizable group, including, for example, a vinyl, acryloyl, methacryloyl, styryl, cyanoacrylate, vinyl ether, vinyl ester, isocyanate, epoxy, and/or derivatives thereof that are polymerizable moieties or a siloxane residue.

In one preferred embodiment of Structure 1, A is a carbon atom bearing two groups $R_A$, $(C(R_A)_2)$, B is a carbon atom bearing two groups $R_B$ $(C(R_B)_2)$, C is a carbon atom bearing two groups $R_C$, $(C(R_C)_2)$, and D is a carbon atom bearing two groups $R_D$, $(C(R_D)_2)$, wherein each $R_A$, $R_B$, $R_C$, and $R_D$ group is independently hydrogen or a substituent such as X above, preferably hydrogen or an organic substituent such as a substituted or unsubstituted alkyl; and X is any independently selected substituent, n varies from 0–3, and $R_O$ is a suitable substituent. In a preferred embodiment, the $R_O$ groups in Structure 1 are independently $R_{CO}$ as in Structure 2.

In a more preferred embodiment of Structure 1, the A, B, C, and D groups are each methylene (—$CH_2$—) as in Structure 2; each X is any independently selected substituent, n varies from 0–3, and each $R_O$ is independently a suitable substituent.

In another more preferred embodiment of Structure 1, the A and C groups are each methylene and B and D groups are carbon bearing two hydrogens or two alkyl groups, each X is independently H or a substituent; and n is 1 on both rings common to the spirocarbon with the proviso that any X substituent in each ring is found on the carbon para (C-4 and C-4') to the indicated oxygen substituent, as in Structure 2, and each $R_O$ is any suitable substituent.

An example of a particularly preferred embodiment is described by Structure 2 wherein $R_1$ and $R_2$ are methyl groups and $R_{CO}$ is a carbocyclic aromatic substituent either substituted or unsubstituted.

Compounds of the present invention, used in a non-racemic mixture or with an enantiomeric excess of one enantiomer, are useful as chiral dopants in liquid-crystal compositions in an effective amount. One or more chiral dopants can be used cumulatively in an effective amount, either of Structure 1 or combined with other types of dopants. Suitably, the compound of Structure 1 can be used in the amount of 0.1 to 20 weight percent, based on the total weight of the liquid-crystal composition, preferably 0.5 to 10 weight percent, more preferably 1 to 6 weight percent. Preferably the non-racemic mixture comprises at least 60 weight percent of one of the enantiomers, based on the weight of both enantiomers, preferably at least 80 weight percent, more preferably greater than 90 weight percent. The enantiomeric excess is greater than 0, preferably greater than 0.6. Most preferably the non-racemic mixture is a substantially or essentially pure enantiomer. As mentioned above, the more pure the enantiomer, the less chiral dopant necessary to obtain the desired HTP and, hence, less chance of incompatibilities or adversely affecting the desired anisotropic properties of the liquid-crystal composition.

Preferably the HTP, on a dopant mole fraction basis, of the compound of Structure 1, when used in a particular liquid crystal composition, is greater than 80, more preferably at least 100, most preferably greater than 100.

Compounds of this invention can be readily prepared by those skilled in the art employing standard chemical transformations. Further, these materials can be isolated in enantiomerically pure form using standard methods including but not limited to: chiral HPLC, chiral synthesis, chemical or chromatographic separation of chiral derivatives of the spirophenol, e.g. via diastereomeric esters, urethanes, carbonates, and the like.

The preparation of the spirophenol derivative of the following substructure 3 has been previously described.

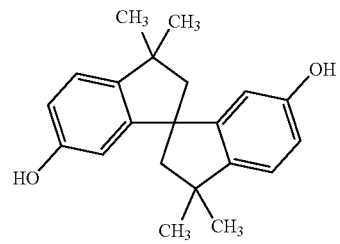

3

See for example a. Gary Ray Faler and Jerry Charles Lynch, EP 264026 A1 19880420 (1988); b. Vladimir Prelog and Davor Bedekovic, *Helvetica Chimica Acta*, 62(7), 2285–302 (1979); c. Bernhard Kohler, Volker Enkelmann, Masao Oda, Silvia Pieraccini, and Gian Piero Spada, Ullrich Scherf, *Chemistry—A European Journal*, 7(14), 3000–3004 (2001); and d. Jens Cuntze and Francois Diederich, *Helvetica Chimica Acta* (1997), 80(3), 897–911. The preparative isolation of the enantiomerically pure derivatives has also been described: a. Romas J. Kazlauskas, *Journal of the American Chemical Society*, 111(13), 4953–9 (1989); and b. Romas J. Kazlauskas, U.S. Pat. No. 4,879,421 (1989);

These and related methods may be employed to prepare enantiomerically enriched samples of the requisite spirophenols.

The use of chiral compounds of the present invention, or a polymerized form thereof, in admixture with a liquid crystal material, can be used for a wide variety of uses, including displays, polarizers, color filters, non-absorptive color filters, liquid crystal pigments for decorative or security purposes or coatings, optical switching, and optical information storage. For example, compositions according to the present invention can be used for making interference pigments with a viewing-angle-dependent color impression in printing inks and surface coatings. The compounds of the present invention can also be used in diagnostic, medical, or cosmetic compositions. For example, liquid-crystal compositions in accordance with the present invention can be used to detect body temperature or to protect the human skin or hair from UV radiation.

The liquid-crystalline composition can comprise STN, TN, chiral nematic, and ferroelectric materials or compounds. Preferably, the material comprises one or more liquid crystal compounds forming a chiral nematic material. The composition can be coated on a substrate, for example, during the manufacture of a display comprising the coated substrate. In one embodiment of a display, the liquid-crystalline composition is disposed between first and second electrodes, wherein the chiral compound according to the present invention is a chiral dopant in liquid crystals.

Novel liquid-crystalline compositions contain one or more chiral compounds of the Structure 1 or 2 as chiral dopants, usually in concentrations of from 0.1 to 10% by weight, based on the total amount of the liquid crystal. The concentration can be selected so that the desired interference hue is formed. Higher concentrations shift the hue into the blue region, and lower ones shift it into the red region.

Preferably, the liquid crystal mixture comprises 2 to 25 compounds, preferably 3 to 15 compounds. Particularly suitable liquid-crystalline compositions are those in which the achiral liquid-crystalline compounds comprise cyclic compounds, for example biphenyls, as will be appreciated by the skilled artisan. Suitable liquid-crystalline compounds are well known to the skilled artisan. The liquid-crystalline compositions can advantageously be used for coating substrates. Examples of suitable substrates are metal surfaces, plastic surfaces, glass or ceramic surfaces or films. Furthermore, the novel liquid-crystalline compositions can be used for the preparation of liquid-crystal displays. To this end, the compositions are, for example, applied to a substrate, preferably a polymeric film, if desired by knife coating or other physical influences. One embodiment of a display in which domains of a cholesteric liquid-crystal composition are dispersed in a polymeric matrix, disposed between electrodes is, for example, disclosed in U.S. Pat. No. 6,236,442 issued May 22, 2001 to Stephenson et al. and U.S. Pat. No. 5,695,682 issued Dec. 9, 1997 to Doane et al., the disclosures of which are incorporated by reference. In one embodiment, a display comprises: (a) a flexible transparent support; (b) a patterned first conductor layer comprising transparent first conductors; (c) a patterned second conductor layer comprising second optionally transparent conductors; and (d) at least one imaging layer comprising domains of polymer-dispersed chiral nematic (cholesteric) liquid-crystal material dispersed in a continuous polymeric matrix, the imaging layer disposed between the first and second conductors. Such chiral nematic liquid-crystal material can exhibit two contrasting stable states, a reflecting planar state and a light-transmissive focal conic state, which two states can be switched from one to the other by application of suitable voltages.

EXAMPLES

1. Preparation of Compounds of the Invention:

The synthesis of representative compounds of the invention, as shown in Scheme 1 below, begins with preparation of racemic Int-2, followed by chiral resolution of this enantiomeric mixture to provide I-1, and finally derivatization of the enantiomerically enriched spirodiphenols I-3. The preparation of 3,3,3',3'-tetramethyl-1,1'-spirobiindan-6,6'-diol using a minor variant of the method described by Faler and Lynch (vide supra). This synthetic route and its subsequent partial enantiomeric resolution are outlined in Scheme 1. The preparation of related, but previously undescribed, nortetramethyl I-2, 1,1'-spirobiindan-6,6'-diol along with preparation of an ester derivative, are outlined in Scheme 2.

Preparation of (±)-Int-1:

Using a minor variant of the procedure of Faler and Lynch (vide supra), a mixture of bis-phenol A (Int-1; CAS 80-05-7; 100 g, 0.438 mole) and methanesulfonic acid (5 mL) were heated at 135° C. for three hours then cautiously poured into 550 mL water with stirring. After stirring a short while the liquid was decanted and the remaining solid diluted with 350 mL water and the stirring continued. This procedure was repeated twice further to provide a semi-solid mass. The damped solid was heated to reflux with 150 mL methylene chloride for one hour then chilled. The solid was collected, washed with minimal cold methylene chloride and ligroin to provide Int-2 as a white solid 29.1 g (65%).

This material proved chromatically homogenous and displayed spectral characteristics consistent with its assigned structure.

Preparation of Diastereomeric Mixture of Int-3 and Int-4 and Isolation of Int-3:

A solution of Int-2 (12.3 g; 40 mmol), triethylamine (TEA; 20 mL, 144 mmol), and 4-dimethylaminopyridine (DMAP; 1 g, 8 mmol) in 200 mL methylene chloride was treated over circa ten minutes with a solution of menthyl chloroformate (CAS 14602-86-9; 18 mL, 84 mmol) in 5 mL methylene chloride. The resulting mixture stirred at ambient temperature for three hours then was washed with dilute hydrochloric acid, dried with sodium sulfate, filtered and concentrated in vacuo. The glassy residue, containing an equimolar mixture of the diastereomers Int-3 and Int-4 as assessed by NMR spectroscopy, was dissolved in 150 mL heptanes. Shortly, crystallization initiated and the slurry stirred at ambient temperature for twenty hours. The slurry was chilled then filtered; the solids washed with minimal cold heptanes and low-boiling ligroin to provide Int-3 as a colorless solid, 9.46 g (35%; 70% based on single diastereomer). This material proved chromatically homogenous and displayed spectral characteristics consistent with its assigned structure. High field NMR detected none of the alternative diastereomer, Int-4.

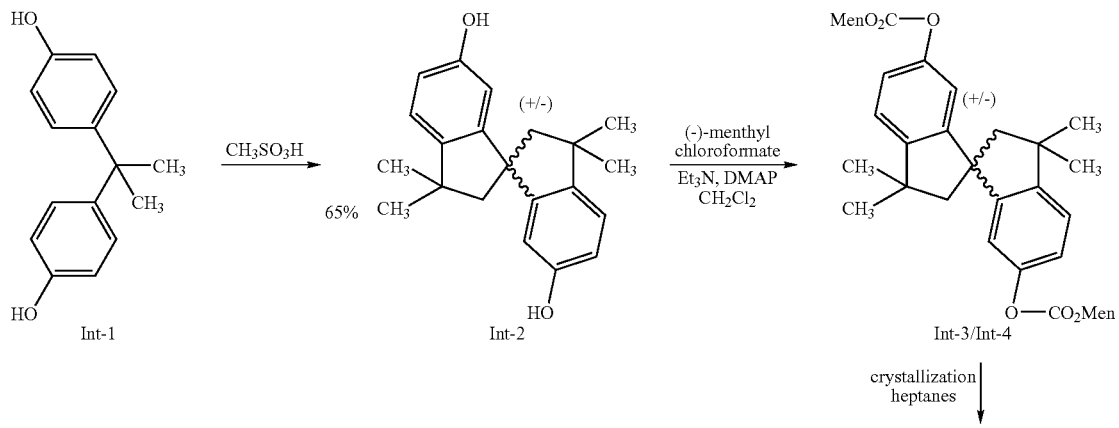

Scheme 1

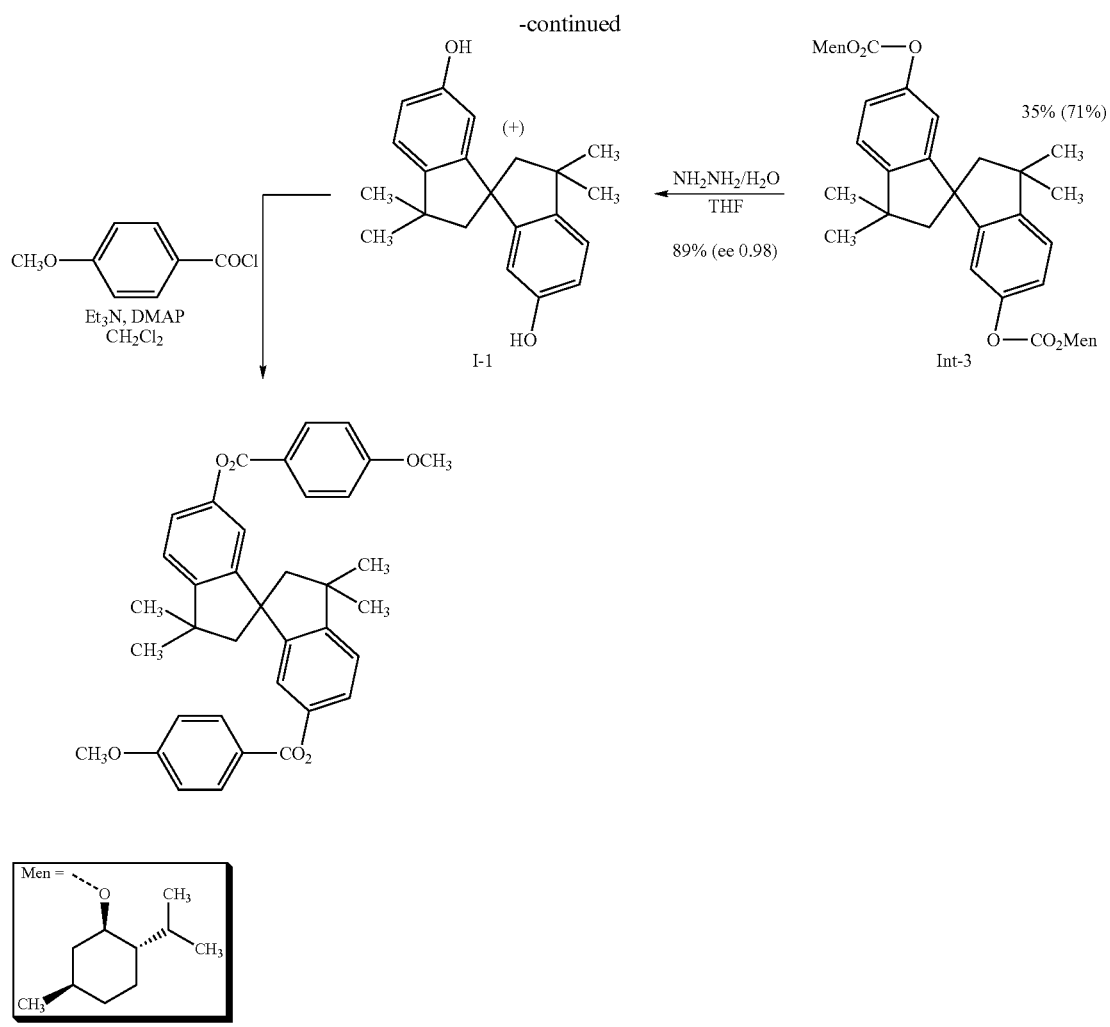

Preparation of (+) I-1:

A solution of Int-3 (9.00 g, 13.4 mmol) and hydrazine monohydrate (4.6 mL, 95 mmol) in 85 mL tetrahydrofuran (THF) was heated at reflux for three hours then portioned between dilute hydrochloric acid and ethyl acetate. The organic layer wash dried with sodium sulfate, filtered and concentrated in vacuo to provide an oil. Two silica gel chromatographies, first eluting with mixture of methylene chloride and ethyl acetate, then secondly, eluting with mixtures of heptanes and isopropyl ether, gave a purified oil. Trituration with IPE/heptanes, followed by filtration and drying, finally yielded Int-1 as a colorless solid, 3.66 g (88.6%). This material proved chromatically homogenous and displayed spectral characteristics consistent with its assigned structure. Chiral HPLC analysis indicate an %ee of >98%; Polarimetry provided $[\alpha]_D^{23}$=+37.4° (methanol, c=0.010).

Preparation of I-3:

A solution of (+)-I-1 (154 mg, 0.50 mmol) and anisoyl chloride (CAS 100-07-2; 0.20 g, 1.2 mmol) in 5.0 mL acetonitrile was treated sequentially with TEA (0.2 mL, 13 mmol) and DMAP (20 mg, 0.2 mmol). The mixture stirred at ambient temperature for two hours then the mixture was partitioned between dilute hydrochloric acid and ethyl acetate. Work afforded an oil, which was purified via silica gel chromatography, eluting with mixtures of heptanes and isopropyl ether. Finally, trituration provided I-3 as a colorless solid, 0.15 g (51%). This material proved chromatically homogenous and displayed spectral characteristics consistent with its assigned structure.

Preparation of Int-7:

A mixture Montmorillonite K10 clay (CAS 1318-93-0; 20 g, dried ≧100° C. in vacuo) and 100 mL xylenes were refluxed under a Dean-Stark trap for twenty minutes, then 1,5-(4-methoxyphenyl)-3-pentanone (Int-6; CAS 74882-32-9, prepared via standard synthetic procedures outlined in Scheme 2; 4.00 g, 13.4 mmol) was added and the reflux continued for twenty hours. The mixture was briefly cooled and then filtered through diatomaceous earth. The solids were washed with toluene (100 mL in portions). The combined filtrates were concentrated in vacuo to provide a crude solid. This material was carefully chromatographed on silica gel, eluting with mixtures of heptanes and ethyl acetate, to provide a purified semi-solid. Trituration of this material with cold isopropyl ether then provided Int-7 as a colorless solid, 0.75 g (20%). This material proved chromatically homogenous and displayed spectral characteristics consistent with its assigned structure.

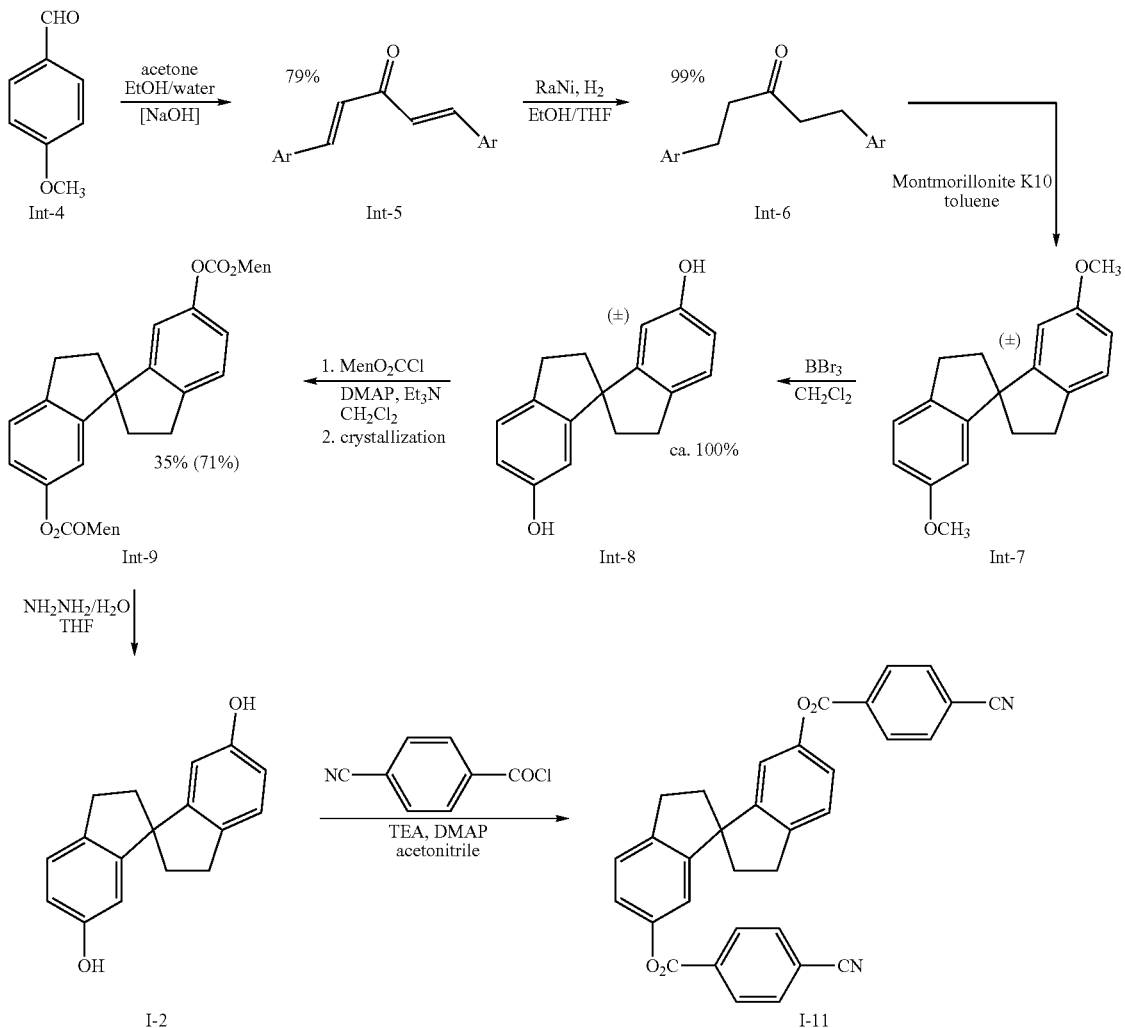

Scheme 2

Preparation of Int-8:

A solution of Int-7 (0.56 g, 2.0 mmol) in 10 mL methylene chloride was chilled in an ice-acetone bath then treated with boron tribromide (0.45 mL, 4.8 mmol). The mixture stirred at ambient temperature for one hour then was cooled and the reaction quenched by the cautious addition of 5 mL water. The organics were separated, dried with sodium sulfate, filtered and concentrated in vacuo. The residue was treated with isopropyl ether and heptane to induce crystal formation. These solvents were removed in vacuo to provide Int-8 as a colorless solid, 0.5 g (circa 100%). This material proved chromatically homogenous and displayed spectral characteristics consistent with its assigned structure.

Preparation of Int-9:

A slurry of Int-8 (0.45 g, 1.8 mmol) in 15 mL methylene chloride, at ambient temperature, was sequentially treated menthyl chloroformate (0.8 mL, 3.7 mmol), triethylamine (0.9 mL, 6.5 mmol) and DMAP (0.05 g, 0.4 mmol). The mixture was stirred at ambient temperature for one hour and then washed with dilute hydrochloric acid. The organics were dried with sodium sulfate, filtered and concentrated in vacuo. The residue was chromatographed on silica gel, eluting with methylene chloride, top provide the expected mixture of diastereomers as a colorless oil, 1.1 g (circa 100%). NMR analysis indicated a equimolar mixture of diastereomers. This residue was dissolved in 15 mL heptanes after which crystallization initiated. The mixture stirred at ambient temperature for thirty minutes then was filtered, to yield Int-9 as a colorless solid, 0.39 g (35%, 71% based on a single diastereomer). This material proved chromatically homogenous and displayed spectral characteristics consistent with its assigned structure. Careful NMR analysis indicated the presence of a single diastereomer.

Preparation of I-2:

A solution of Int-9 (0.35 g, 0.57 mmol) in 7.5 mL THF was treated with hydrazine monohydrate (0.25 mL, 5.2 mmol) then heated at reflux for thirty minutes. Additional hydrazine monohydrate was added (0.15 mL, 3.1 mmol) and mix heated another hour. The mix stirred at ambient temperature overnight then was partitioned between dilute hydrochloric acid and ethyl acetate. The organic layer was dried with sodium sulfate, filtered and concentrated in vacuo to provide a glassy residue. Silica gel chromatography, eluting with mixtures of methylene chloride and ethyl acetate, gave a purified oil. This oil was dissolved ethyl acetate then washed with dilute aqueous sodium hydroxide. The aqueous layer was acidified with hydrochloric acid and extracted with ethyl acetate. The organics were dried, filtered, and concentrated to provide I-2 as a colorless oil, 0.14 g ((100%). This material proved chromatically homogenous and displayed spectral characteristics consistent with its assigned structure.

Preparation of I-11:

A solution of I-2 (50 mg, 0.12 mmol) and 4-cyanobenzoyl chloride (CAS 6068-72-0; 70 mg, 0.42 mmol) in 5 mL acetonitrile at ambient temperature was sequentially treated with triethylamine (0.10 mL, 0.72 mmol) and DMAP (5 mg, 0.04 mmol). The mixture stirred for forty-five minutes then was partitioned between dilute hydrochloric acid and ethyl acetate. The organic layer was dried with sodium sulfate, filtered and concentrated in vacuo to provide a glassy residue. This material was chromatographed on silica gel, eluting with methylene chloride, to afford I-11 as a colorless solid, 90 mg, (90%). This material proved chromatically homogenous and displayed spectral characteristics consistent with its assigned structure.

Example 1

Several enantiomerically pure derivatives of the invention were prepared (vide infra) and known amounts of these compounds combined with the commercially available liquid crystalline compound 4-n-pentyl-4'-cyanobiphenyl, 5CB, having the following structure:

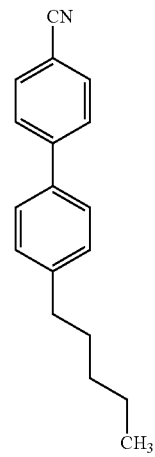

5CB
40817-08-1
4-Cyano-4'-pentylbiphenyl

The mixture was heated above its clearing point, thoroughly mixed and allowed to cool to ambient temperature. The pitches of these samples were then measured either from standard reflectance response curves or by the method of Dogic and Fraden (vide supra). The HTP's (β) of these samples, on a mole fraction basis, were then calculated as described above. Results of this experiment are found in Table 1 showing the HTP's in 5CB at ambient temperatures.

TABLE 1

| Compound | β ($\mu m^{-1}$) |
|---|---|
| I-3 | 0.1 |
| I-6 | 0.4 |
| I-7 | 30 |

Example 2

Several enantiomerically pure derivatives of the invention were prepared (vide supra) and known amounts of these compounds combined with the commercially available liquid crystalline mixture BL087 (described as a mixture of 5CB (25–40%), the structurally related 2CB wherein the n-pentyl group is replaced by an ethyl group (10–25%), and a proprietary LC mixture (35–65%)) available from Merck KGaA, Darmstadt, Germany. The mixture was heated above its clearing point, thoroughly mixed and allowed to cool to ambient temperature. The pitches of these samples were then measured either from standard reflectance response curves or by the method of Dogic and Fraden (vide supra). The HTP (β) of these samples was then calculated as described above, except on a weight percent basis. Results of this experiment are found in Table 2 below showing HTP's in 5CB at ambient temperatures.

TABLE 2

| Compound | β ($\mu m^{-1}$) weight % |
|---|---|
| I-3 | 0.61 |
| I-5 | 0.63 |
| I-6 | 0.53 |
| I-8 | 0.60 |
| I-10 | 0.63 |
| I-12 | 0.14 |
| I-13 | 0.17 |

The invention has been described in detail with particular reference to certain preferred embodiments thereof, but it will be understood that variations and modifications can be effected within the spirit and scope of the invention

What is claimed is:

1. A liquid-crystalline composition comprising as a chiral dopant admixed with a liquid-crystal material, at least one chiral compound, or a polymerized form thereof, represented by the following structure:

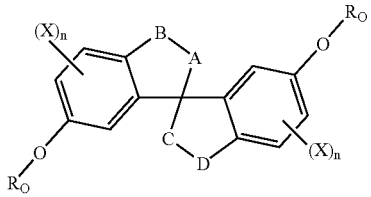

wherein A, B, C, and D are independently selected divalent groups, the X groups are independently selected substituents, the n subscripts are independently 0, 1, 2, or 3, and the $R_O$ groups are independently hydrogen or a substituent capping each oxygen, and wherein any two X and/or $R_O$ groups can optionally form a fused ring and the two $R_O$ groups can optionally connect to form a bridge, wherein Structure 1 excludes macrocyclic compounds containing two or more structural units based on Structure 1.

2. The composition of claim 1 wherein A, B, C, and D is independently selected from the group consisting of methylene, oxygen, sulfur, sulfoxyl, sulfonyl, carbonyl, monosubstituted nitrogen (N—R), and di-substituted carbon ($R_1$—C—$R_2$), wherein R, $R_1$ and $R_2$ are independently hydrogen or a substituent and any two R, $R_1$ and $R_2$ groups on the same ring in said structure can optionally form a fused ring.

3. The composition of claim 2 wherein A, B, C, and D are independently methylene or di-substituted carbon ($R_1$—C—$R_2$).

4. The composition of claim 1 wherein A and B are the same, respectively, as C and D.

5. The composition of claim 1 wherein each X substituent is independently selected from the group consisting of oxygen-containing organic substituents and/or a carbon-containing substituents.

6. The composition of claim 5 wherein each X is independently selected from the group consisting of alkoxy, aryloxy, carboalkyl (O—C(=O)R), carboaryl (O—C(=O)Ar), carboalkoxy (O—C(=O)OR), carboaryloxy (O—C(=O)OAr), alkyl groups of about 1–20 carbons, cycloalkyl groups of about 1–20 carbons, aryl groups of about 6–20 carbons, alkaryl groups of about 6–20 carbons, carboalkoxy (C—C(=O)OR), carboaryloxy (C—C(=O)OAr), aryl or alkyl ketones (C—C(=O)R) or (C—C(=O)Ar), all either substituted or unsubstituted, or any two members of the X and $R_0$ groups on a ring may be joined to form a fused ring; Ar is an aryl group and R is an independently hydrogen or substituent.

7. The composition of claim 1 represented by the following structure:

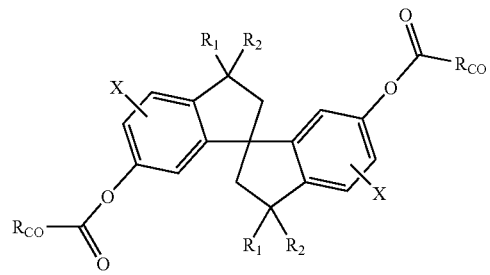

wherein each $R_{CO}$ is an independently selected substituent and each $R_1$ and $R_2$ are independently hydrogen or an alkyl substituent.

8. The composition of claim 7 wherein $R_{CO}$ is aryl, alkyl, cycloalkyl, alkaryl or heterocyclic, all either substituted or unsubstituted.

9. The composition of claim 1 wherein the compound is a polymerization product of compounds of Structure 1 that are capable of polymerization.

10. The liquid-crystalline composition of claim 1 further comprising a polymer binder in which domains of the liquid crystal are dispersed.

11. The liquid-crystalline composition of claim 1 wherein the liquid-crystalline composition is STN, TN, chiral nematic, or ferroelectric.

12. The liquid-crystalline composition of claim 1 wherein the liquid-crystalline composition is chiral nematic.

13. A coated substrate comprising the liquid-crystalline composition of claim 1.

14. A display comprising the liquid-crystalline composition of claim 1 wherein the composition is disposed between first and second electrodes.

15. The display of claim 14 wherein the liquid-crystalline composition is bistable and dispersed in the form of domains in a polymeric matrix.

* * * * *